United States Patent
Wiley et al.

(10) Patent No.: US 10,413,700 B2
(45) Date of Patent: Sep. 17, 2019

(54) SECURABLE PROCEDURE KIT

(71) Applicant: C. R. Bard, Inc., Murray Hill, NJ (US)

(72) Inventors: Martha R. Wiley, Salt Lake City, UT (US); Heather R. Murphy, Herriman, UT (US); Angela D. Grosklags, Cottonwood Heights, UT (US); Eddie K. Burnside, Bountiful, UT (US); Kelly J. Christian, Draper, UT (US); Bradley W. Zentgraf, Salt Lake City, UT (US); Russell L. Bjorklund, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 396 days.

(21) Appl. No.: 14/512,235

(22) Filed: Oct. 10, 2014

(65) Prior Publication Data

US 2015/0101616 A1    Apr. 16, 2015

Related U.S. Application Data

(60) Provisional application No. 61/890,111, filed on Oct. 11, 2013.

(51) Int. Cl.
*A61B 46/23* (2016.01)
*A61M 25/00* (2006.01)
(Continued)

(52) U.S. Cl.
CPC .......... *A61M 25/002* (2013.01); *A61B 46/23* (2016.02); *A61B 50/20* (2016.02); *A61B 50/22* (2016.02);
(Continued)

(58) Field of Classification Search
CPC ......... A61B 46/00; A61B 46/20; A61B 46/23; A61B 2046/234
(Continued)

(56) References Cited

U.S. PATENT DOCUMENTS 2,172,455 A    9/1939  Max
2,265,680 A   12/1941  Alberta
(Continued)

FOREIGN PATENT DOCUMENTS

EP    3055995 B1    6/2018
GB    836258 A    6/1960
(Continued)

OTHER PUBLICATIONS

PCT/US14/60172 filed Oct. 10, 2014 International Search Report and Written Opinion dated Mar. 25, 2015.
(Continued)

*Primary Examiner* — Keri J Nelson

(74) *Attorney, Agent, or Firm* — Rutan & Tucker, LLP

(57) ABSTRACT

A procedure kit that removably retains components to be used during a medical procedure, such as the insertion of a catheter into a patient, is disclosed. The procedure kit is securable to a surface or structure such that the kit is positioned as desired by the clinician, thus minimizing chances that the kit will fall to the ground or undesirably move. In one embodiment, the procedure kit comprises a body defining a plurality of pockets that are sized to removably receive therein components for use in the medical procedure, an openable flap that covers at least a portion of the pockets; and an adhesive portion included on a portion of the body to enable the procedure kit to be secured to a structure or surface proximate to the patient, such as the sterile drape covering the patient.

27 Claims, 14 Drawing Sheets

(51) Int. Cl.
*A61B 50/20* (2016.01)
*A61B 50/30* (2016.01)
*A61B 50/22* (2016.01)
*A61B 50/31* (2016.01)
*A61B 50/00* (2016.01)

(52) U.S. Cl.
CPC .............. *A61B 50/30* (2016.02); *A61B 50/31* (2016.02); *A61B 50/00* (2016.02); *A61B 2046/234* (2016.02); *A61B 2046/236* (2016.02); *A61B 2050/002* (2016.02); *A61B 2050/0065* (2016.02); *A61B 2050/0089* (2016.02); *A61B 2050/314* (2016.02); *A61B 2050/318* (2016.02)

(58) Field of Classification Search
USPC .................. 128/849, 852; 206/363–366, 370
See application file for complete search history.

(56) References Cited

U.S. PATENT DOCUMENTS

| | | | |
|---|---|---|---|
| 2,733,113 | A * | 1/1956 | Humbargar .......... A47B 81/007 |
| | | | 206/45.24 |
| 3,017,990 | A | 1/1962 | Sol |
| 3,062,371 | A | 11/1962 | Donald |
| 3,095,088 | A | 6/1963 | Blaikie et al. |
| 3,119,495 | A | 1/1964 | Pratt |
| 3,137,387 | A | 6/1964 | Overment |
| 3,162,307 | A | 12/1964 | Regan, Jr. |
| 3,318,510 | A * | 5/1967 | Quarles, III ........... B65D 27/34 |
| | | | 206/804 |
| 3,503,391 | A | 3/1970 | Melges |
| 3,650,393 | A | 3/1972 | Reiss et al. |
| 3,749,233 | A | 7/1973 | McCormick, Jr. |
| 3,768,971 | A * | 10/1973 | Fishpaw ................ A61B 50/00 |
| | | | 206/572 |
| 3,780,857 | A | 12/1973 | Rosano, Jr. et al. |
| 3,791,382 | A | 2/1974 | Collins |
| 3,817,190 | A * | 6/1974 | Evangelista ............. A47B 5/04 |
| | | | 108/44 |
| 3,884,412 | A | 5/1975 | Price |
| 3,952,738 | A | 4/1976 | Krzewinski |
| 4,342,390 | A | 8/1982 | Mitchell et al. |
| D268,811 | S | 5/1983 | Black |
| D271,422 | S | 11/1983 | Breland |
| 4,415,089 | A * | 11/1983 | Ruffa ................ A61B 17/06061 |
| | | | 206/363 |
| D272,600 | S | 2/1984 | Kubas |
| 4,466,659 | A * | 8/1984 | Carpentier ................ A47C 7/70 |
| | | | 108/149 |
| 4,476,860 | A * | 10/1984 | Collins .................. A61B 46/23 |
| | | | 128/852 |
| 4,522,302 | A | 6/1985 | Paikoff |
| 4,523,679 | A | 6/1985 | Paikoff et al. |
| D292,024 | S | 9/1987 | Hanssen et al. |
| 4,844,259 | A | 7/1989 | Glowczewskie, Jr. et al. |
| 5,022,521 | A | 6/1991 | Kane |
| 5,074,316 | A | 12/1991 | Dowdy |
| 5,082,111 | A | 1/1992 | Corbitt, Jr. et al. |
| D325,518 | S | 4/1992 | Matkovich |
| 5,203,457 | A | 4/1993 | Garcia |
| 5,749,842 | A | 5/1998 | Cheong et al. |
| 5,816,253 | A | 10/1998 | Sosebee |
| 5,879,620 | A | 3/1999 | Cohen |
| 5,931,303 | A | 8/1999 | Salvadori |
| 5,931,304 | A | 8/1999 | Hammond |
| 5,947,296 | A | 9/1999 | Castora |
| 6,016,915 | A | 1/2000 | Almond |
| 6,149,302 | A | 11/2000 | Taheri |
| 6,308,875 | B1 * | 10/2001 | Almo .................. A41D 13/0012 |
| | | | 2/251 |
| 6,412,639 | B1 | 7/2002 | Hickey |
| 6,436,085 | B1 * | 8/2002 | Lauer .................... A61M 39/10 |
| | | | 604/408 |
| 6,460,702 | B2 | 10/2002 | Hammond |
| 6,595,361 | B2 | 7/2003 | Sugama |
| 6,837,027 | B2 | 1/2005 | Hickey |
| 6,957,738 | B2 | 10/2005 | Hammond |
| D540,665 | S | 4/2007 | Gupta et al. |
| 7,273,148 | B2 | 9/2007 | Perry et al. |
| 7,293,654 | B1 | 11/2007 | Wilson, Jr. et al. |
| 7,331,463 | B2 | 2/2008 | Hickey |
| D589,347 | S | 3/2009 | Dacey |
| 7,624,869 | B2 | 12/2009 | Primer |
| 7,628,275 | B2 | 12/2009 | Smith |
| D609,819 | S | 2/2010 | Tomes et al. |
| 7,673,754 | B2 | 3/2010 | Wilson, Jr. et al. |
| D623,765 | S | 9/2010 | Tomes et al. |
| 7,798,323 | B1 | 9/2010 | McCann et al. |
| D636,894 | S | 4/2011 | Tomes et al. |
| 7,967,139 | B2 | 6/2011 | Brinker |
| D650,912 | S | 12/2011 | Tomes et al. |
| D657,124 | S | 4/2012 | Dacey et al. |
| 8,167,130 | B2 | 5/2012 | Holstein |
| 8,240,471 | B2 | 8/2012 | Brinker |
| 8,261,963 | B2 | 9/2012 | Gaynor et al. |
| 8,302,775 | B2 | 11/2012 | Holstein |
| 8,448,786 | B2 | 5/2013 | Tomes et al. |
| 8,464,722 | B2 | 6/2013 | Chua |
| 8,485,419 | B2 | 7/2013 | Gaynor et al. |
| 8,631,935 | B2 | 1/2014 | Tomes et al. |
| 8,678,190 | B2 | 3/2014 | Tomes et al. |
| 8,685,189 | B2 | 4/2014 | Pamperin et al. |
| D704,856 | S | 5/2014 | Tomes et al. |
| 8,727,957 | B2 | 5/2014 | Smith et al. |
| 8,746,452 | B2 | 6/2014 | Tomes et al. |
| 8,789,702 | B1 | 7/2014 | Shingyouchi-Hall |
| 8,852,502 | B2 | 10/2014 | Landgrebe et al. |
| 8,875,940 | B2 | 11/2014 | Danchisin et al. |
| 9,162,781 | B2 | 10/2015 | Lien |
| 9,174,782 | B2 | 11/2015 | Gaynor et al. |
| 9,254,176 | B2 | 2/2016 | Hartley |
| D752,452 | S | 3/2016 | Kearns et al. |
| 9,283,352 | B2 | 3/2016 | Tomes et al. |
| 9,296,535 | B2 | 3/2016 | Gaynor et al. |
| 9,327,042 | B2 | 5/2016 | Griesbach, III et al. |
| D764,943 | S | 8/2016 | Murray et al. |
| 9,522,753 | B2 | 12/2016 | Tomes et al. |
| 9,693,756 | B2 | 7/2017 | Tomes et al. |
| 9,745,088 | B2 | 8/2017 | Tomes et al. |
| 9,795,761 | B2 | 10/2017 | Lockwood et al. |
| 9,808,400 | B2 | 11/2017 | Tomes et al. |
| 9,808,596 | B2 | 11/2017 | Tomes et al. |
| 2002/0088729 | A1 | 7/2002 | Urbanski |
| 2004/0158186 | A1 | 8/2004 | Hall |
| 2004/0256283 | A1 | 12/2004 | Jasper et al. |
| 2005/0211590 | A1 | 9/2005 | McClure et al. |
| 2006/0206992 | A1 | 9/2006 | Godshaw et al. |
| 2006/0231443 | A1 | 10/2006 | Jonasson et al. |
| 2007/0260166 | A1 | 11/2007 | Johnson |
| 2008/0007706 | A1 | 1/2008 | Reisinger et al. |
| 2008/0120945 | A1 | 5/2008 | Holbrook et al. |
| 2008/0283426 | A1 | 11/2008 | Primer et al. |
| 2009/0230000 | A1 | 9/2009 | Sackos |
| 2009/0236259 | A1 | 9/2009 | Hicks |
| 2010/0274205 | A1 | 10/2010 | Morelli et al. |
| 2010/0307941 | A1 | 12/2010 | Tomes et al. |
| 2010/0307942 | A1 | 12/2010 | Tomes et al. |
| 2010/0311026 | A1 | 12/2010 | Tomes et al. |
| 2011/0232234 | A1 | 9/2011 | Lockwood et al. |
| 2011/0233079 | A1 | 9/2011 | Macinnes et al. |
| 2011/0284012 | A1 * | 11/2011 | McCollough .......... A61B 46/23 |
| | | | 128/852 |
| 2011/0284410 | A1 | 11/2011 | Lockwood |
| 2011/0290260 | A1 | 12/2011 | Tomes et al. |
| 2011/0290262 | A1 | 12/2011 | Tomes et al. |
| 2012/0065566 | A1 | 3/2012 | Bar-Natan |
| 2012/0145589 | A1 | 6/2012 | Macinnes et al. |
| 2012/0150123 | A1 | 6/2012 | Lawrence et al. |
| 2012/0168334 | A1 | 7/2012 | Wittrock |
| 2012/0202000 | A1 | 8/2012 | Bricker et al. |
| 2012/0222686 | A1 | 9/2012 | Lockwood et al. |
| 2012/0298114 | A1 | 11/2012 | Landsman et al. |

(56) References Cited

U.S. PATENT DOCUMENTS

| | | | |
|---|---|---|---|
| 2012/0318706 A1 | 12/2012 | Holstein | |
| 2012/0325704 A1* | 12/2012 | Kerns | A61B 50/33 |
| | | | 206/370 |
| 2013/0037440 A1 | 2/2013 | Danchisin et al. | |
| 2013/0056011 A1* | 3/2013 | Taub | A61B 46/00 |
| | | | 128/852 |
| 2013/0081355 A1 | 4/2013 | Gaynor et al. | |
| 2013/0092724 A1 | 4/2013 | Gaynor et al. | |
| 2013/0111852 A1 | 5/2013 | Farmer et al. | |
| 2013/0152946 A1 | 6/2013 | Sosnowski | |
| 2013/0269713 A1 | 10/2013 | Bui et al. | |
| 2013/0277248 A1 | 10/2013 | Tomes et al. | |
| 2014/0021087 A1 | 1/2014 | Adler et al. | |
| 2014/0138269 A1* | 5/2014 | Ghosh | A61B 19/0271 |
| | | | 206/370 |
| 2014/0142465 A1 | 5/2014 | Tomes et al. | |
| 2014/0231287 A1 | 8/2014 | Tomes et al. | |
| 2014/0231288 A1 | 8/2014 | Tomes et al. | |
| 2014/0257250 A1* | 9/2014 | Palmer | A61M 25/002 |
| | | | 604/544 |
| 2014/0262851 A1 | 9/2014 | Adler et al. | |
| 2014/0272873 A1 | 9/2014 | Svensson et al. | |
| 2015/0027922 A1 | 1/2015 | Fresco | |
| 2015/0033673 A1 | 2/2015 | Lien | |
| 2015/0034521 A1 | 2/2015 | Lien | |
| 2015/0048103 A1 | 2/2015 | Danchisin et al. | |
| 2015/0083627 A1 | 3/2015 | Gorman | |
| 2015/0238351 A1 | 8/2015 | Tsimbler | |
| 2015/0258304 A1 | 9/2015 | Tomes et al. | |
| 2015/0266649 A1 | 9/2015 | Sweeney | |
| 2015/0327934 A1 | 11/2015 | Thomas et al. | |
| 2015/0335855 A1 | 11/2015 | Tomes et al. | |
| 2015/0367011 A1 | 12/2015 | Kalmon et al. | |
| 2016/0022853 A1 | 1/2016 | Hajime et al. | |
| 2016/0095663 A1 | 4/2016 | Richart | |
| 2016/0135895 A1 | 5/2016 | Faasse et al. | |
| 2016/0166800 A1 | 6/2016 | Tomes et al. | |
| 2016/0167871 A1 | 6/2016 | Nickell | |
| 2016/0187309 A1 | 6/2016 | Kang et al. | |
| 2016/0193444 A1 | 7/2016 | Tomes et al. | |
| 2016/0271283 A1 | 9/2016 | Kozin | |
| 2017/0232226 A1 | 8/2017 | Loui et al. | |
| 2017/0296282 A1 | 10/2017 | Turturro et al. | |
| 2017/0296283 A1 | 10/2017 | Turturro et al. | |
| 2017/0296284 A1 | 10/2017 | Turturro et al. | |
| 2017/0319183 A1 | 11/2017 | Tomes et al. | |
| 2017/0368302 A1 | 12/2017 | Brooks et al. | |

FOREIGN PATENT DOCUMENTS

| | | |
|---|---|---|
| GB | 2396550 A | 6/2004 |
| WO | 95/06449 A1 | 3/1995 |
| WO | 2010/128554 A1 | 11/2010 |
| WO | 2011/025486 A1 | 3/2011 |
| WO | 2011131953 A1 | 10/2011 |
| WO | 2013120182 A1 | 8/2013 |
| WO | 2015054660 | 4/2015 |
| WO | 2016/033089 A1 | 3/2016 |
| WO | 2017/139680 A1 | 8/2017 |

OTHER PUBLICATIONS

EP 14851523.2 filed Mar. 31, 2016 Extended European Search Report dated Apr. 5, 2017.

PCT/US2017/017528 filed Feb. 10, 2017 International Search Report and Written Opinion dated Jun. 21, 2017.

Thompson, H; "Optimizing Package Design for EtO Sterilization"; 12,35 https://web.archive.org/web/20160112004508/http://www.mddionline.com/article/optimizing-package-design-eto-sterilization; Jan. 12, 2006 'downloaded from the World Wide Web, Jun. 6, 2017]; figure; 1st paragraph.

U.S. Appl. No. 15/430,349, filed Feb. 10, 2017 Non-Final Office Action dated Sep. 14, 2018.

U.S. Appl. No. 15/430,349, filed Feb. 10, 2017 Restriction Requirement dated Jul. 12, 2018.

* cited by examiner

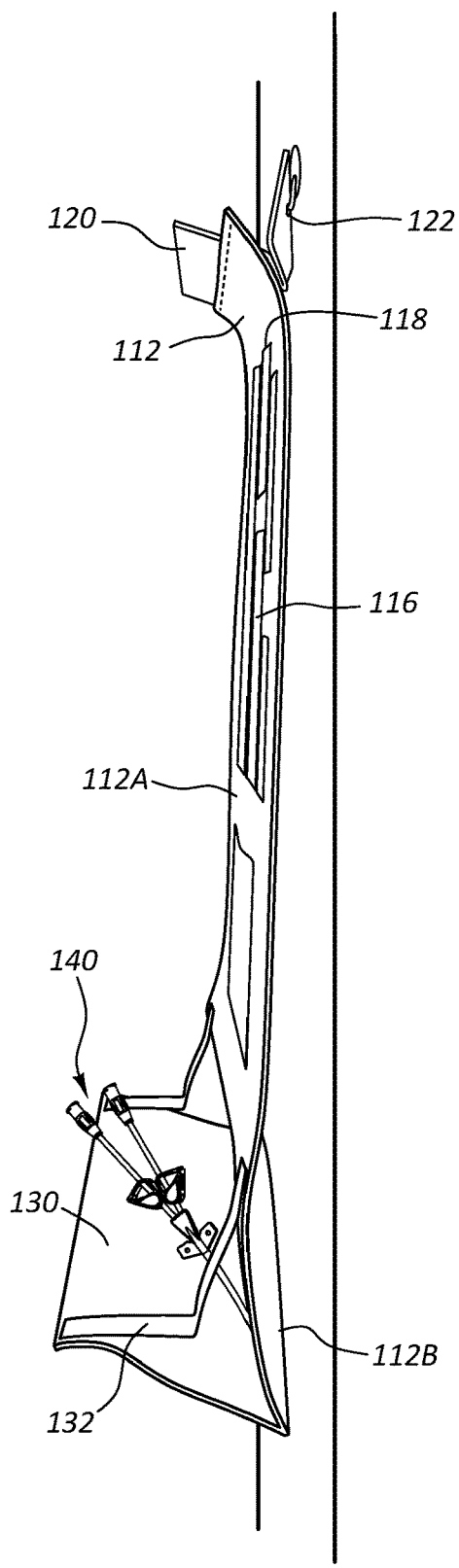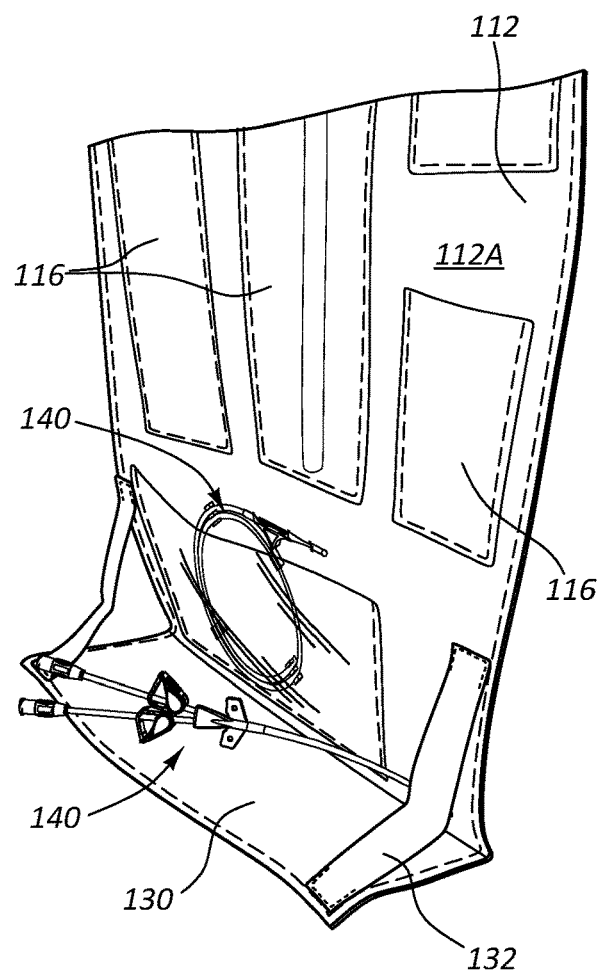
FIG. 6B
FIG. 6C

SECURABLE PROCEDURE KIT

CROSS-REFERENCE TO RELATED APPLICATIONS

This application claims the benefit of U.S. Provisional Application No. 61/890,111, filed Oct. 11, 2013, and titled "Suspendable Procedure Kit," which is incorporated herein by reference in its entirety.

BRIEF SUMMARY

Briefly summarized, embodiments of the present invention are directed to a procedure kit that is used to removably retain components to be used during a medical procedure, such as the insertion of a catheter into a patient. The procedure kit is securable to a surface or structure such that the kit is positioned as desired by the clinician, thus minimizing chances that the kit will fall to the ground or undesirably move. In one embodiment, for instance, the procedure kit can be adhesively secured to a sterile drape covering the patient during the medical procedure. Placement of the procedure kit as described ensures that its contents are easily accessible by the clinician during the procedure.

Thus, in one embodiment, the procedure kit comprises a body defining a plurality of pockets that are sized to removably receive therein components for use in the medical procedure, an openable flap that covers at least a portion of the pockets; and an adhesive portion included on a portion of the body to enable the procedure kit to be secured to a structure or surface proximate to the patient, such as the sterile drape covering the patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 6A-6C are various views of a securable procedure kit according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a procedure kit that is used to removably retain components to be used during a medical procedure, such as the insertion of a catheter into a patient, for instance. The procedure kit is securable to a surface or structure such that the kit is positioned as desired by the clinician, thus minimizing chances that the kit will fall to the ground or undesirably move. In one embodiment, for instance, the procedure kit can be secured to a sterile drape covering the patient during the medical procedure. Placement of the procedure kit as described ensures that its contents are easily accessible by the clinician during the procedure.

Figure 1A:
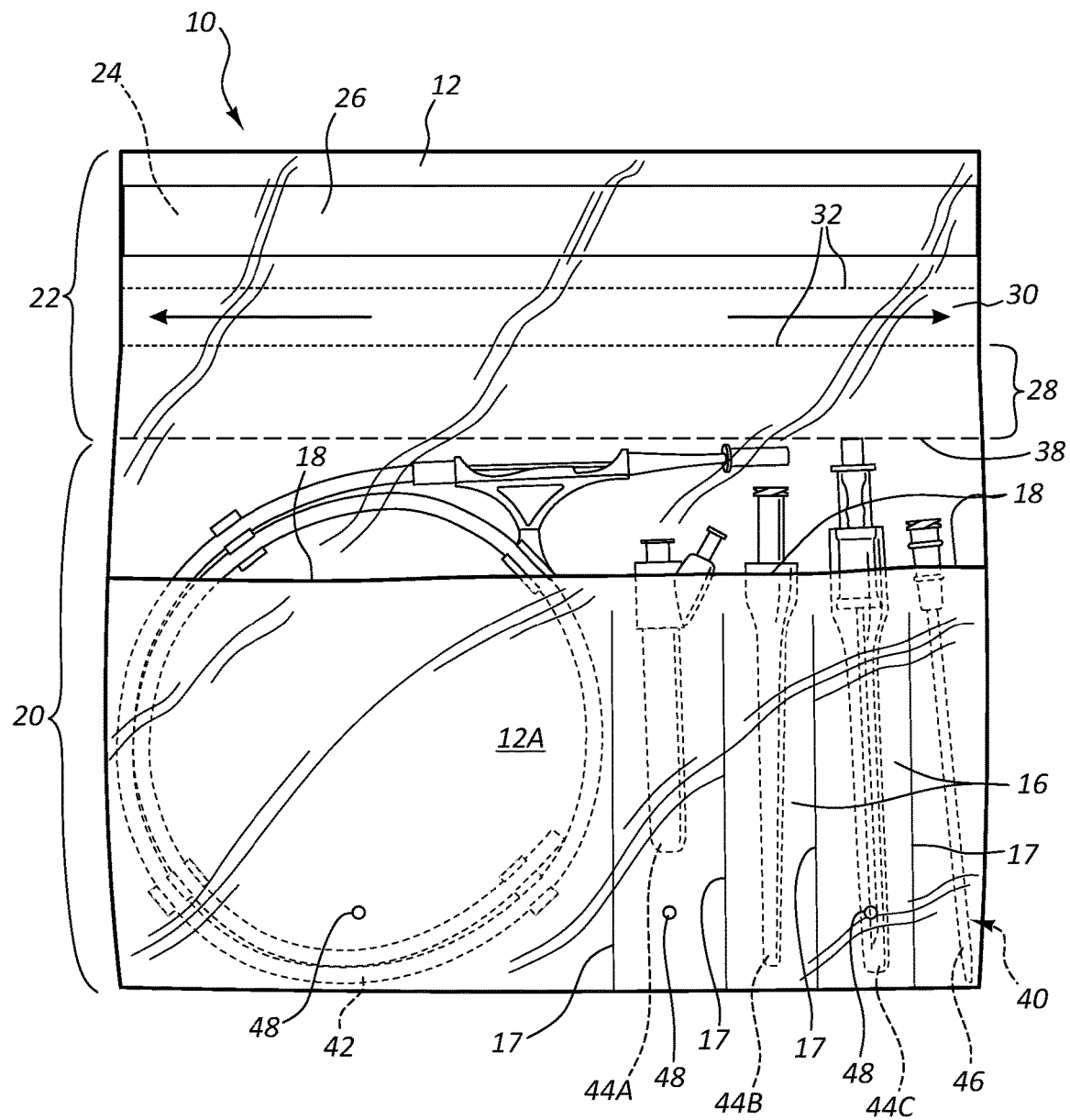
FIGS. 1A-1C are various views of a securable procedure kit, according to one embodiment.
Figure 1B:
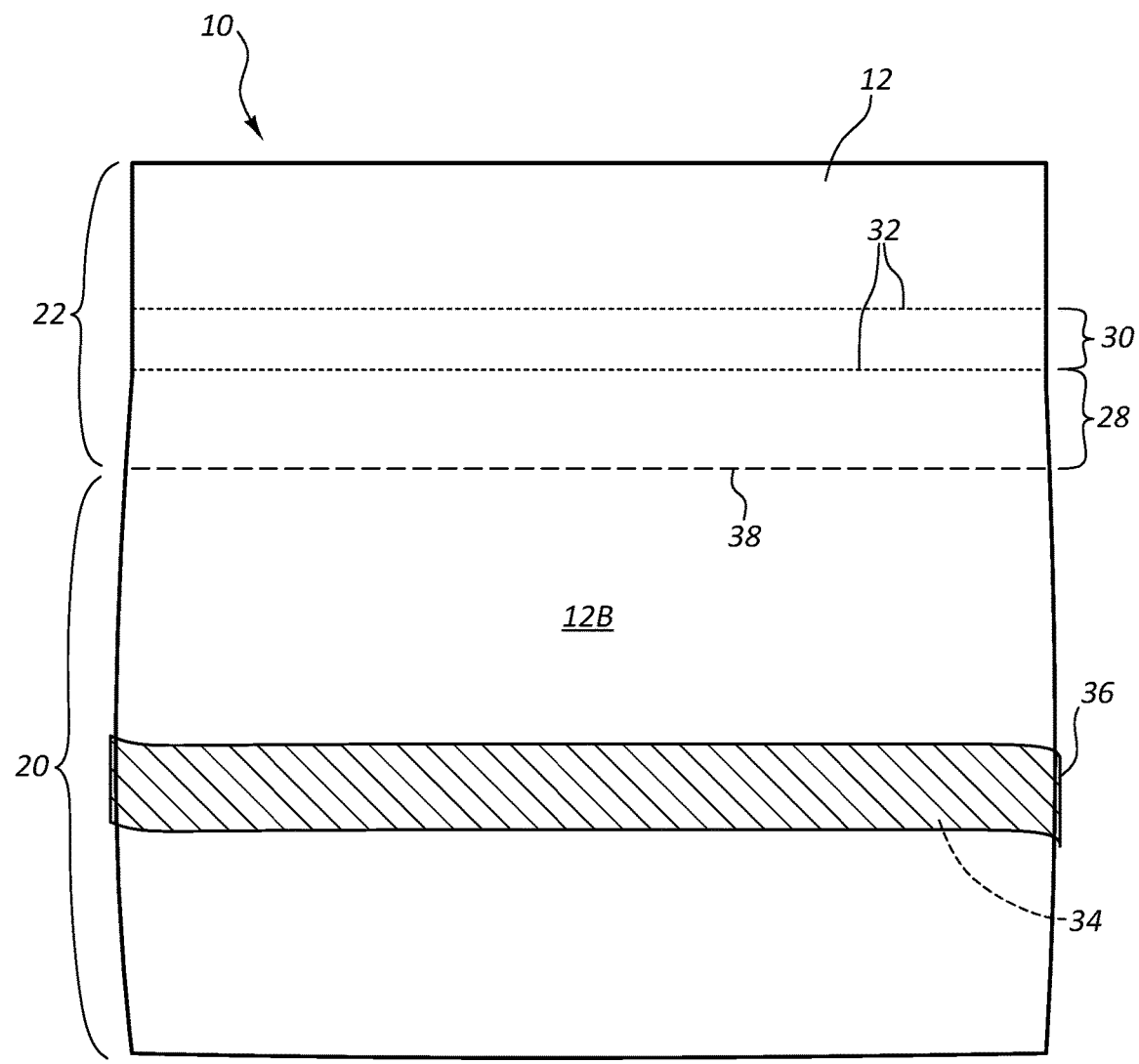
Figure 1C:
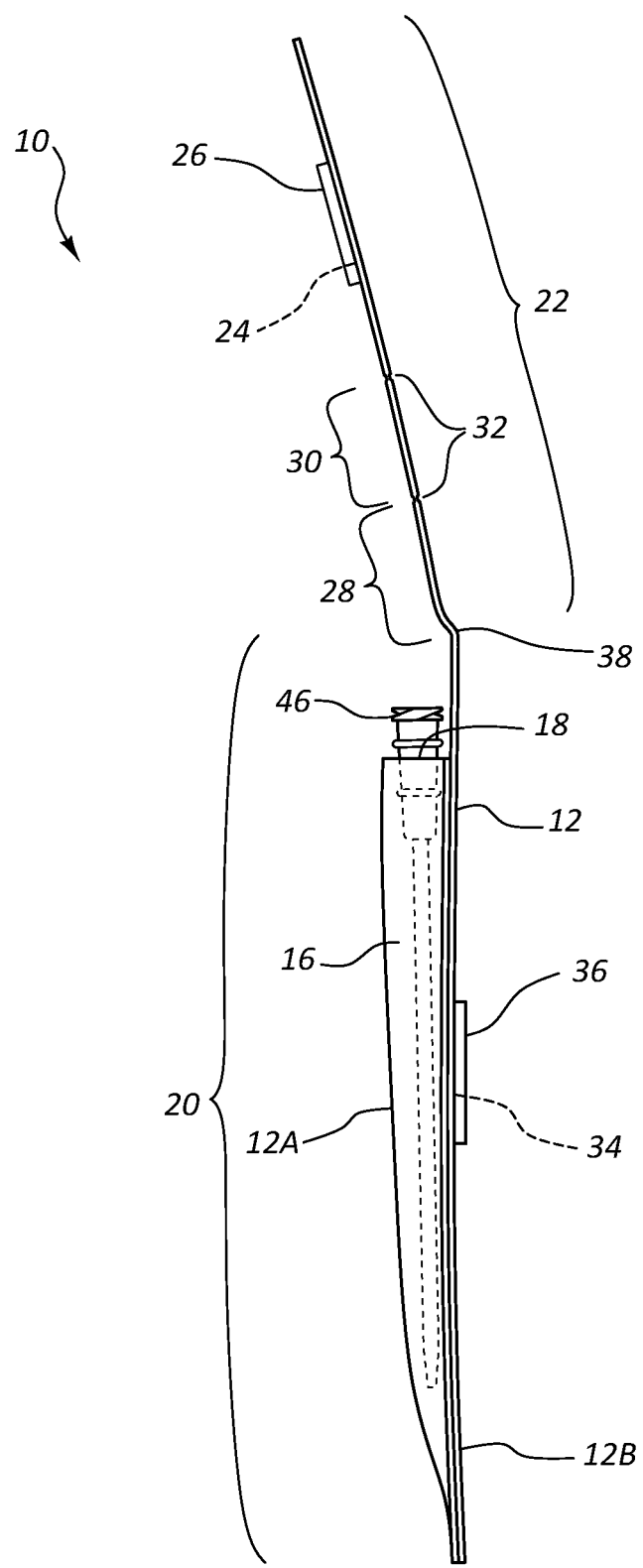

Reference is first made to FIGS. 1A-1C, which depict various views of a securable procedure kit ("procedure kit" or "kit"), generally designated at 10, according to one embodiment. As shown, the kit 10 includes a body, or package, 12 that is flexible, generally flat, and translucent in the present embodiment, though other package configurations, including more rigid and opaque designs, are contemplated. In one embodiment, the package includes a polyethylene film of a thickness of about 4 mils, though other materials and thicknesses can be employed, including both high and low-density polyethylene, and molded, extruded, or thermo-formed plastic.

The package 12 is substantially flat and defines both a front face 12A and a rear face 12B. A plurality of pockets 16 is defined by the package 12 such that each pocket includes an opening 18 on the front face 12A. The pockets 16 are sized and arranged to removably receive therein a particular component to be used in a medical procedure for which the kit is configured. For instance, in the present embodiment the kit 10 includes a plurality of kit components 40 for assisting with the placement of a central catheter into the vasculature of a patient, including a guidewire/guidewire hoop assembly 42, various needles 44—namely needles 44A, 44B, and 44C—and a dilator 46. In the present embodiment, for instance, the needle 44A includes a 22 gauge×1.5 inch safety hypodermic needle for Lidocaine administration, needle 44B includes a 21 gauge×2¾ inch finder needle for accessing a subcutaneous vein, needle 44C includes an 18 gauge introducer needle, and the dilator 46 includes an 8 French dilator. Of course, a variety of other components can be included in the procedure kit.

As the guidewire/guidewire hoop assembly 42 is larger relative the other kit components 40, its respective pocket 16 is also sized larger. Of course, the pockets 16 can be configured in different ways to accommodate components of different sizes, shapes, number, etc. The pockets 16 can also be positioned in other areas or faces of the kit package 12.

The pockets 16 are separated from one another by partitions 17 that are formed in one embodiment by heat sealing/heat bonding a portion of the front face 12A to the rear face 12B of the package 12 to form the respective partition. Other methods for forming separations between the pockets 16 can also be used.

The package 12 further defines a lower package portion 20 in which the pockets 16 are formed in the present embodiment, and a cover flap 22 that is configured to fold over and cover a portion of the lower package portion 20. The cover flap 22 includes a permanent adhesive strip 24 including a permanent adhesive configured to join the cover flap with a portion of the lower package portion 20 in such a way that separation of the adhered-to portions is relatively difficult to achieve. A release strip 26 is placed over the permanent adhesive strip 24 to isolate it until joining of the cover flap 22 with the lower package portion 20 is desired, as will be described further below.

The cover flap 22 further includes an access flap 28 that is adjacent to a fold line 38, the fold line being the line at which the cover flap is folded over on to the lower package portion 20. A tear-away portion 30 including a pair of perforations 32 is included adjacent the access flap 28. The use of these features is described further below.

A non-permanent adhesive strip 34 is disposed on the rear face 12B of the lower package portion 20 to enable the package 12 to be adhered to a structure or desired location so as to be readily accessible by a clinician using the kit during a catheter insertion into the patient or other medical procedure, as will be described. A release strip 36 is disposed over the non-permanent adhesive strip 34 to protect it until ready for use. The location and type of adhesives used for the both the permanent and non-permanent adhesive strips 24 and 34 can vary according to application. Generally, low-tack adhesives, such as silicone adhesives or adhesives including acrylate copolymer microspheres, are suitable for the non-permanent adhesive strip 34, while acrylic adhesives is but one substance that can be used for the permanent adhesive strip 24. In one embodiment, the permanent adhesive strip 24 includes a styrene-butadiene-styrene ("SBS") block copolymer, while the non-permanent adhesive strip 34 includes a styrene-isoprene-styrene ("SIS") block copolymer. Other thermoplastic elastomers can also be employed for the permanent and non-permanent adhesive strips.

In one embodiment, the procedure kit body 12 can be manufactured from a length of suitable material, folded and bonded about the edges of the body to define the general configuration shown in FIG. 1A, with the front face 12A defining a single, large pocket area. The partitions 17 are then formed to define the individual pockets 16. The permanent and non-permanent adhesive strips 24 and 34 can then be applied to the body 12, and the respective release strips 26 and 36 applied to cover the adhesive strips. The various components 40 can then be inserted into the respective pockets 16.

Figure 2:
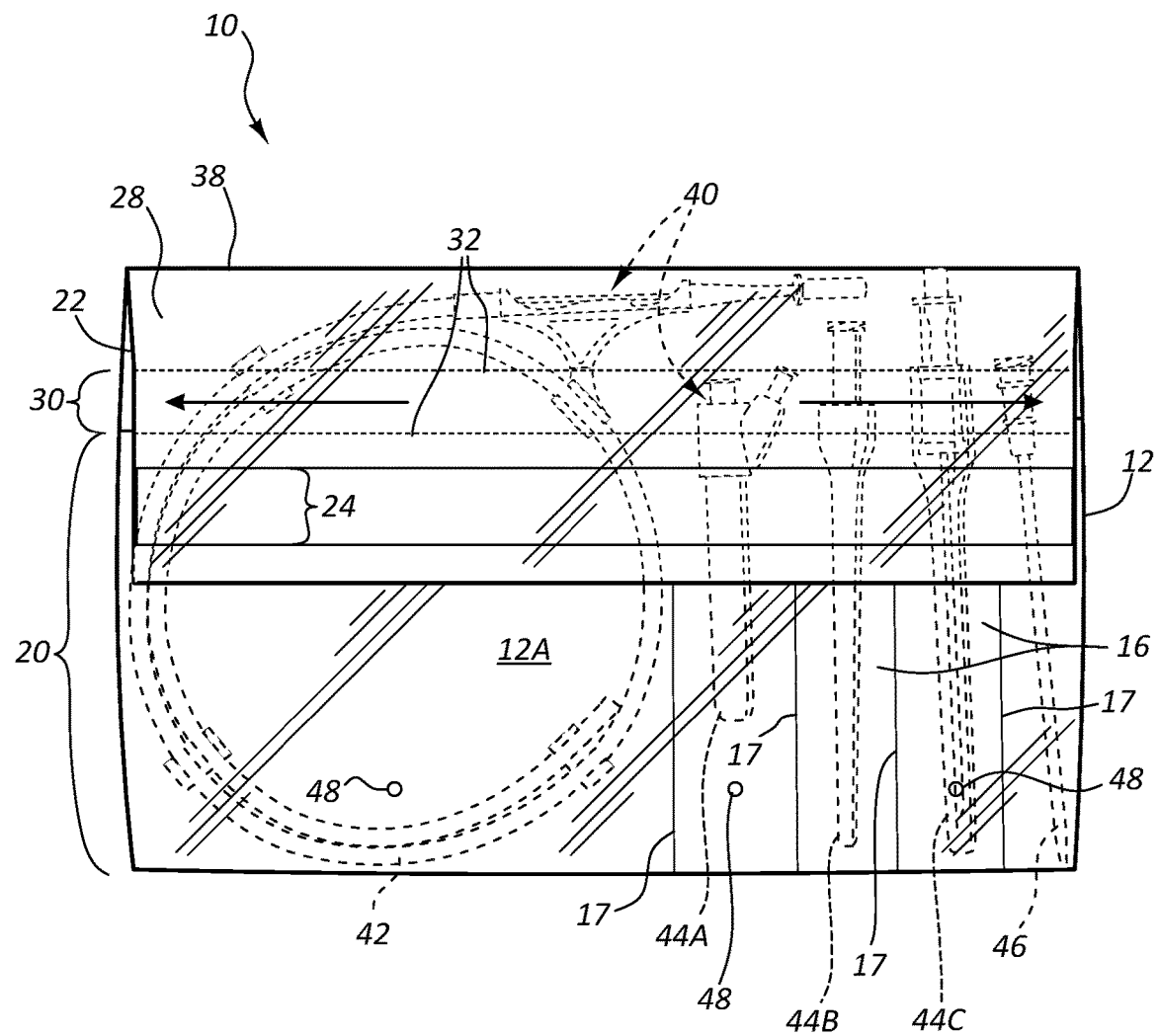
FIG. 2 is a front view of the procedure kit of FIGS. 1A-1C in a first configuration.

Further to the above-described manufacture of the procedure kit 10, FIG. 2 depicts the procedure kit in a first configuration after manufacture and packaging, but prior to use by a clinician. As shown, the cover flap 22 has been folded over at the fold line 38 during manufacture so as to cover the openings 18 of each of the pockets 16 included on the lower package portion 20. The release strip 26 has been removed from covering the permanent adhesive strip 24 such that the permanent adhesive strip of the cover flap 22 bonds with a corresponding adjacent portion of the lower package portion 20 so as to substantially permanently join therewith. In this way, the components 40 disposed in the pockets 16 are protected so as to prevent their escape from their respective pocket and the package 12. The kit 10 in the first configuration shown in FIG. 2 is ready for sterilization procedures to eliminate any microbial of other contamination therein. To that end, holes 48 are included in the package 12 to enable sterilizing agents to penetrate into the pockets 16, in the present embodiment. Note that in one embodiment the permanent adhesive can be included on the lower package portion 20 instead of the cover flap, or in another suitable location.

Figure 3:
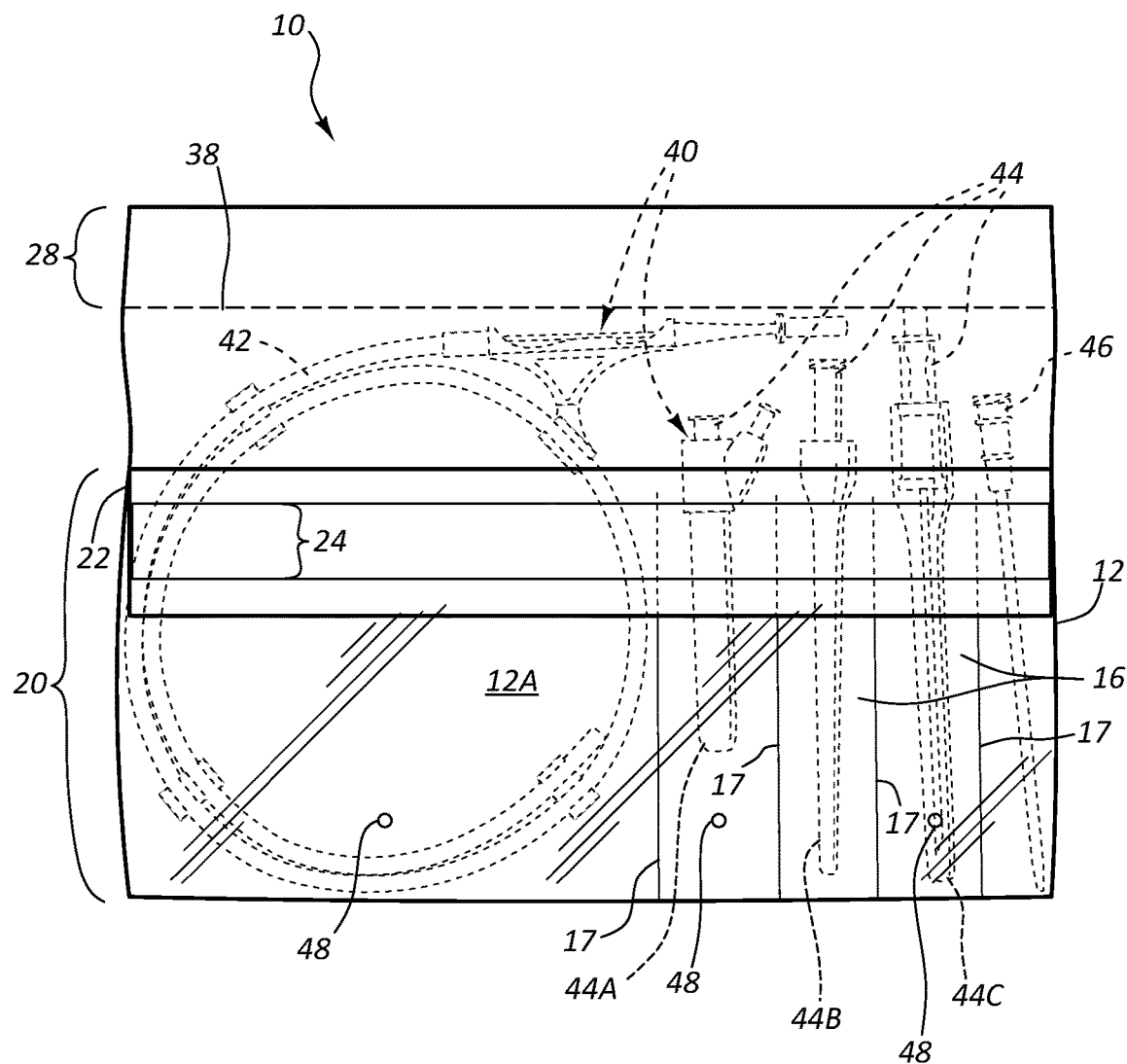
FIG. 3 is a front view of the procedure kit of FIGS. 1A-1C in a second configuration.

FIG. 3 depicts the kit 10 of FIG. 2, but in a second configuration, with the kit open and ready for use. As shown, the tear-away portion 30 has been removed from the cover flap 22 via pulling action such that it separates from the cover flap at the perforations 32 (FIG. 2). This enables the access flap 28 of the cover flap 22 to be flipped up at the fold line 38 to expose the openings 18 of the pockets 16 and enable access to the components 40 disposed therein.

Figure 4:
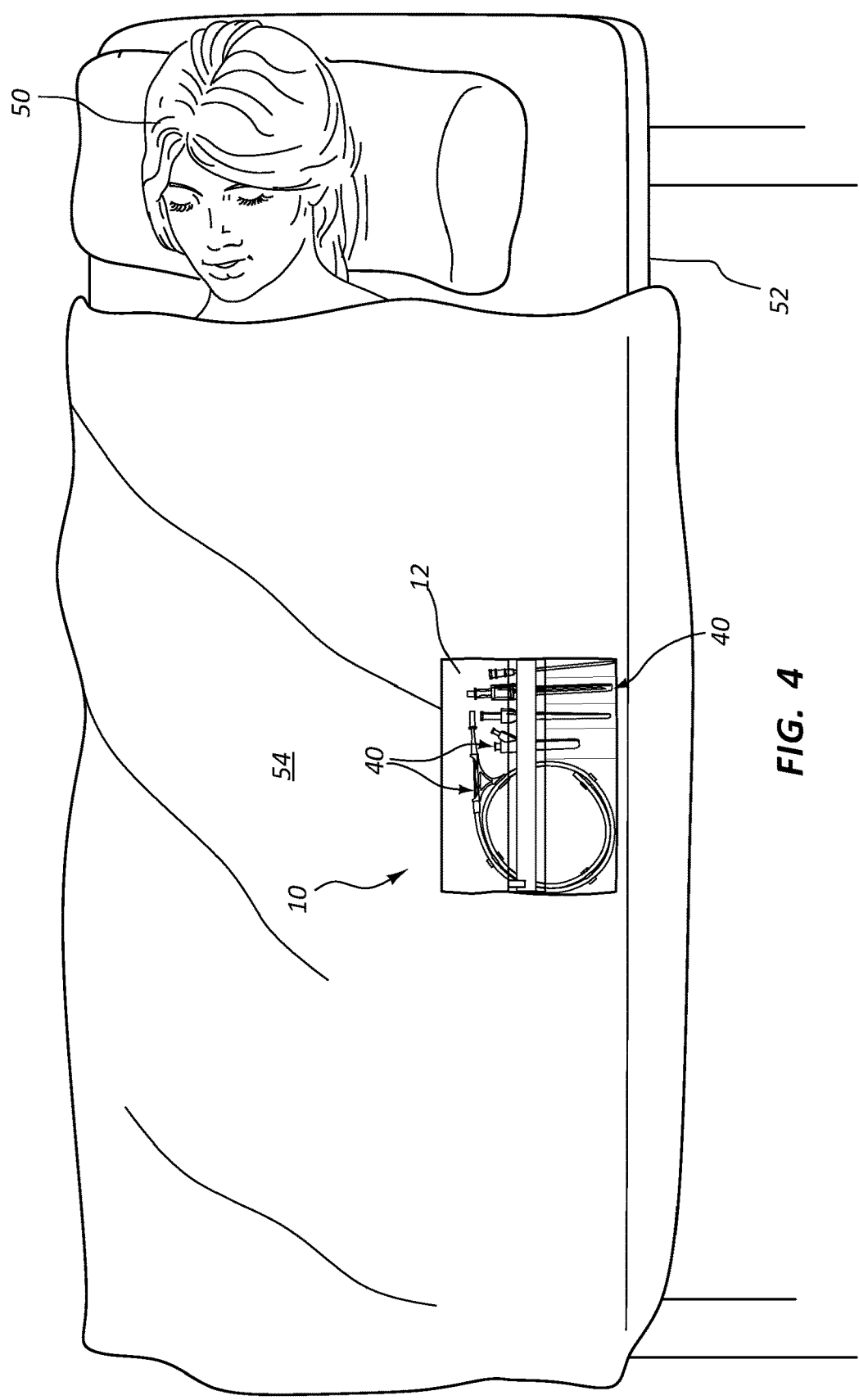
FIG. 4 shows a procedure kit in use according to one embodiment.

FIG. 4 depicts use of the kit 10 in the second configuration of FIG. 3. As shown, the kit 10 is opened, as depicted in FIG. 3. The procedure kit 10 is shown affixed to a drape 54 covering a patient 50 lying in a bed 52 such that the kit stays in place atop the patient 50 and is readily accessible by a clinician performing a medical procedure on the patient. To affix the kit 10 to the drape 54 as shown, the release strip 36 is first removed from the package 12 (FIG. 1B) in order to expose the non-permanent adhesive strip 34 on the rear face 12B of the package 12. The package 12 can then be placed against a structure or surface, and the non-permanent adhesive strip 34 adhered to the structure or surface to keep the kit in place. When use of the kit 10 is no longer needed, the package 12 can be removed by pulling to disengage the non-permanent adhesive strip 34 from the structure or surface.

Note that the above serves as merely one example of placement of the procedure kit 10 for use in a medical procedure. Other locations for placement of the procedure kit 10 can be contemplated.

Figure 5:
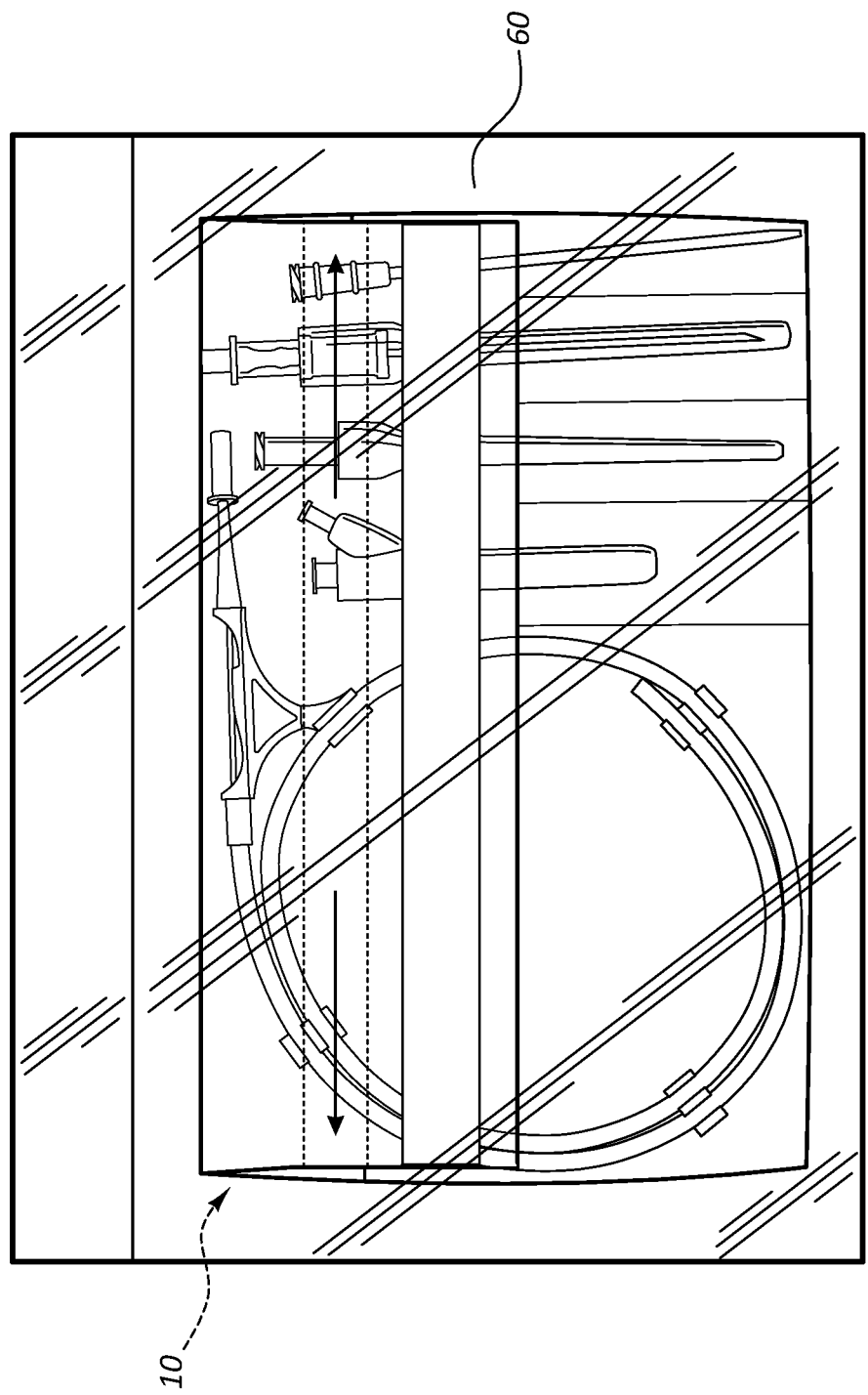
FIG. 5 shows a procedure kit included in an outer pouch according to one embodiment.

FIG. 5 shows that, in one embodiment, the kit 10 can be disposed before use in an outer pouch 60, so as to maintain sterility of the kit. As such, after placement in the outer pouch 60, the kit 10 and pouch can be subjected to suitable sterilization procedures, such as ethylene oxide sterilization, for instance. In this case, the outer pouch 60 can include a suitably transmissive membrane, such as flashspun high density polyethylene fiber material.

Figure 6A:
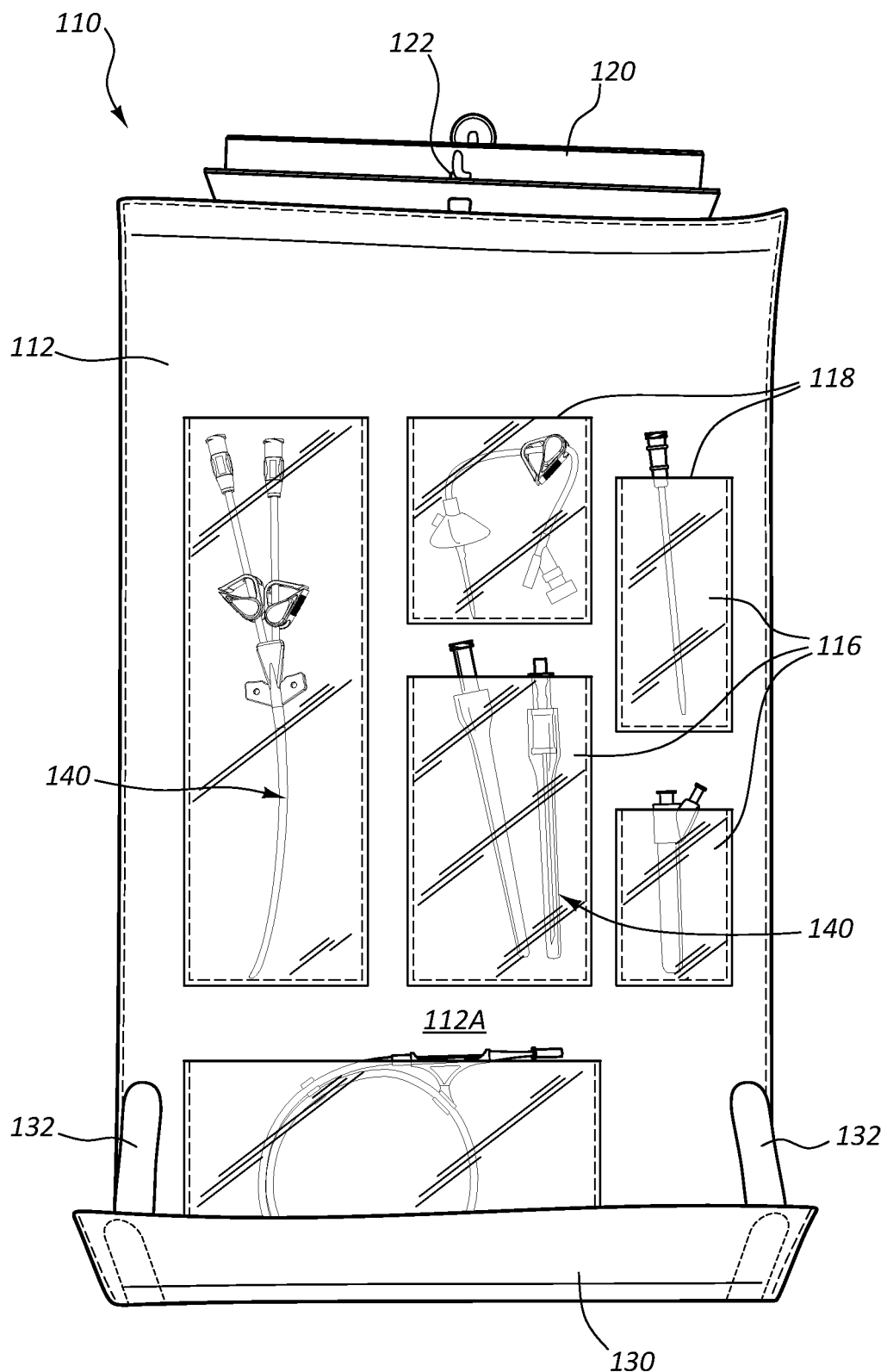

FIGS. 6A-6C depict details of a securable procedure kit ("kit") 110 according to another embodiment. As shown, the kit 10 includes a body 112 that is generally flat, flexible, and rectangularly shaped, though these configurations can be modified according to the desired application for which the kit will be employed. In one embodiment the body 112 includes a suitable thermoplastic, poly tissue, woven material, or other medically accepted material.

The kit body 112 includes a rear face 112B, and a front face 112A on which are disposed a plurality of pockets 116 that are each shaped and sized to removably retain therein one or more of a plurality of components 140 that may be needed for the medical procedure. Examples of such components vary according to procedure, but can include in one embodiment a catheter, needles, cutting devices, syringes, etc. A variety of pocket configurations, including different numbers and sizes of pockets, is possible. Each pocket includes a pocket opening 118 for inserting/removing components. The pockets 116 can include the same material as that of the kit body 112, or can be formed of another material, such as a mesh material, for instance.

A securing component, or hanger portion 120, is included for enabling the kit 110 to be hung for access thereto during a medical procedure. The hanger portion 120 includes in the present embodiment a hole 122 for hanging the kit 110 on a hook or other suitable component. The hanger portion can include other modes of securing/supporting the procedure kit, as will be seen further below. The hanger portion 120 also serves in one embodiment as a stiffening component to enable the kit body 112 to substantially retain its form when hung from an I.V. pole or other location.

The kit body 112 further includes a fold-out tray 130 supported by two support arms 132 at the bottom of the kit 110, though the tray could be located in other positions. The tray 130 provides a place where one or more of the components 140 can be temporarily stored or stowed after use, as shown in FIGS. 6B and 6C. The tray 130 can also serves as a catch tray for catching components if they should inadvertently fall from the pockets 116. The tray 130 and support arms 132 can fold flat when no components 140 are disposed therein so as to enable the kit 110 to be stored in a substantially flat configuration. In one embodiment, the tray 130 can include side portions and/or other structures to help retain components therein.

Figure 7:
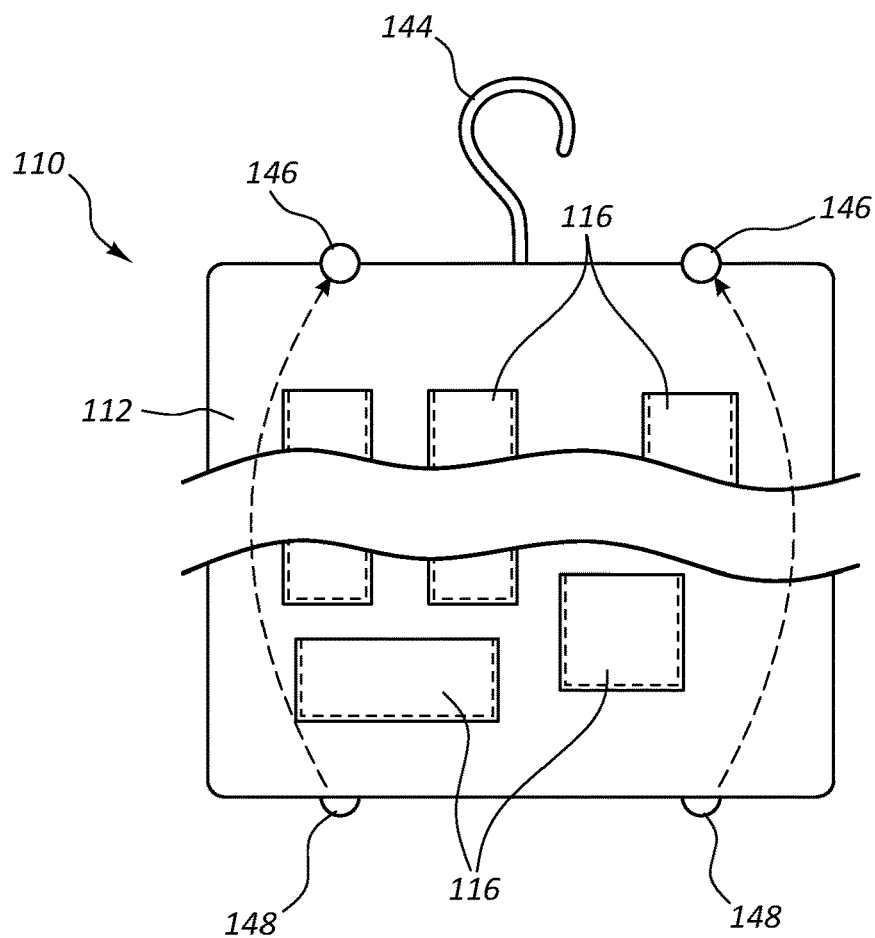
FIG. 7 is a truncated front view of a securable procedure kit according to one embodiment.

FIG. 7 depicts the procedure kit 110 including another example of a securing component for securing the kit to a structure, according to one embodiment. As shown, the securing component includes a hanger hook 144 suitable for suspending the kit 110 from an I.V. pole or other location in a hospital/procedure room, for instance. The kit 110 in FIG. 7 further includes two buttons 146 and corresponding button holes 148 as non-limiting examples of fasteners that can be used to secure the kit body 112 in a folded state for storage or disposal, for instance. The location, number, and type of fasteners can vary from what is shown and described herein. For instance, snaps may be used for the fasteners.

Figure 8:
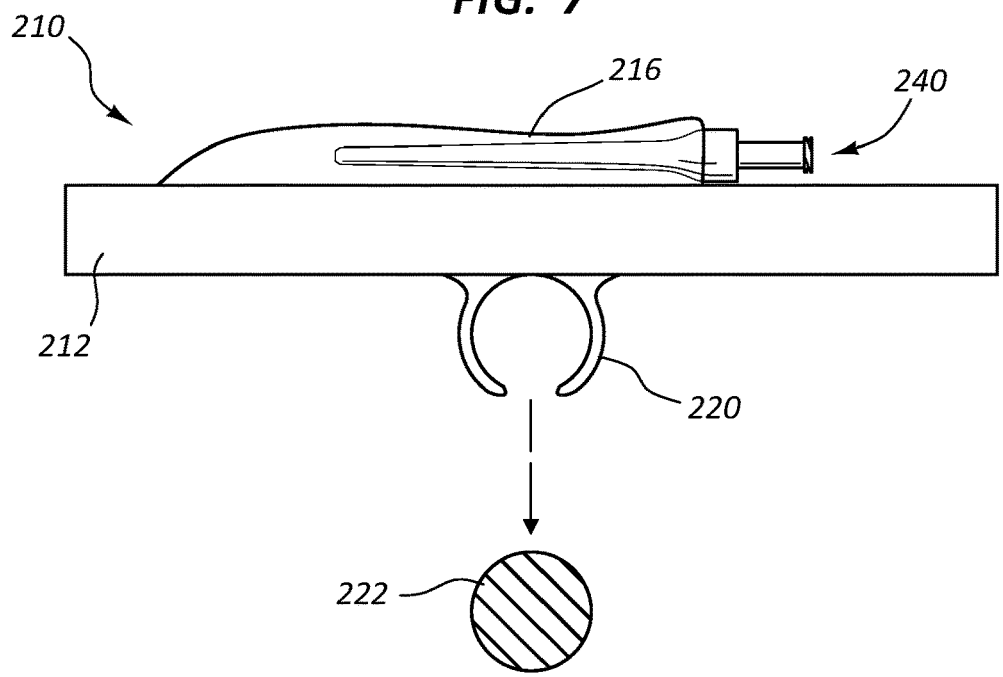
FIG. 8 is a side view of a securable procedure kit according to one embodiment.

FIG. 8 depicts details of a securable procedure kit ("kit") 210 according to one embodiment, including a substantially rigid or semi-rigid base, or body, 212 on which is included one or more pockets 216 in which kit components 240 are removably disposed. A "c"-type clip 220 is included on an underside portion of the body 212 of the kit 210 and is sized for releasably snap-fitting on to a rail or pole, such as a bed rail 222, as shown. The clip 220 thus serves as a securing component for the procedure kit 210 includes a thermoplastic or other suitable material that is resilient sufficient to receive therein the bed rail 222 without breaking. The particular configuration, size, and placement of the clip 220 on the kit body 212 can vary from what is shown and described herein. In other embodiments, other modes for securing the kit to a structure may be employed, including clamps, etc.

Figure 9:
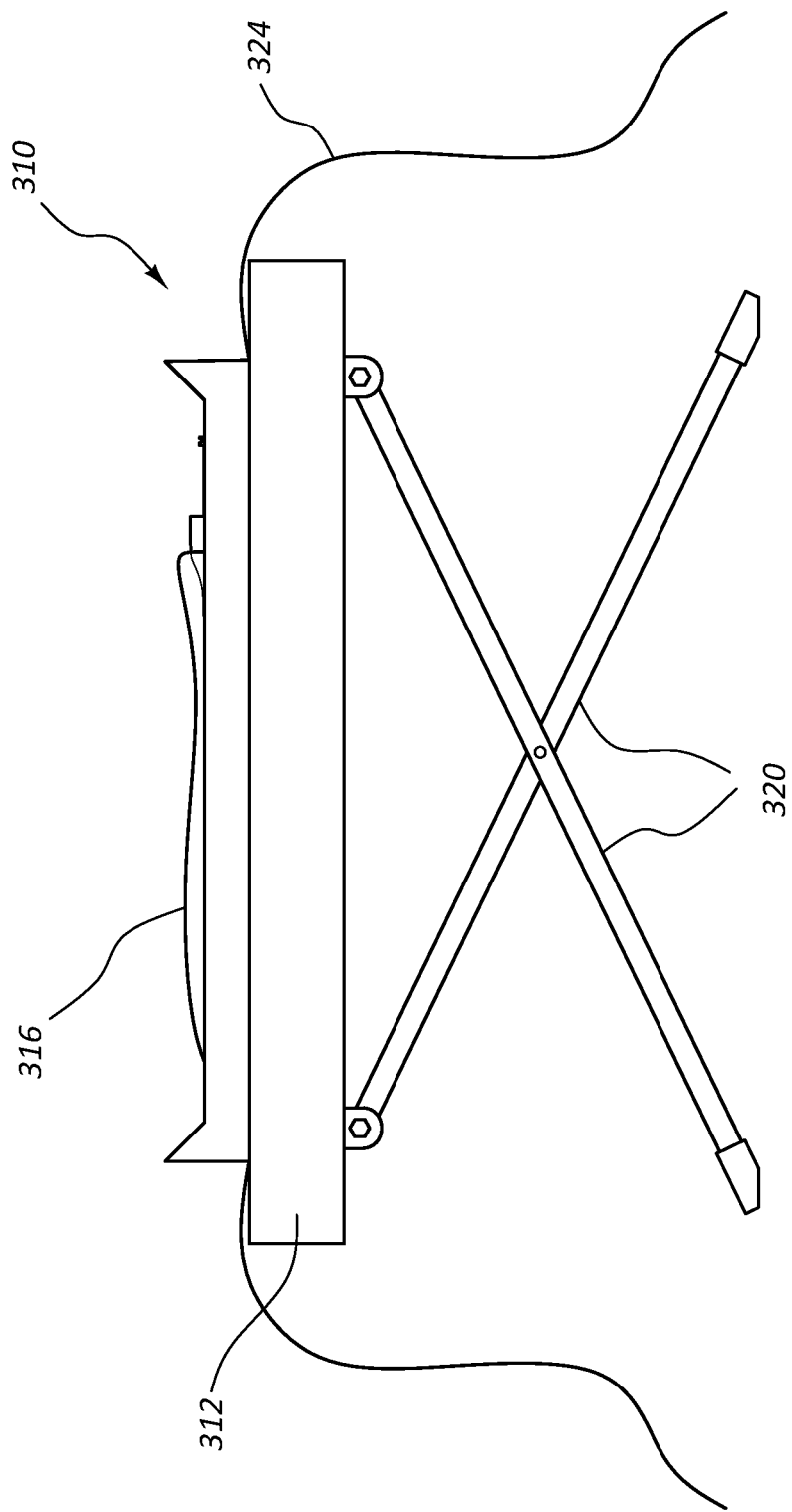
FIG. 9 is a side view of a securable procedure kit according to one embodiment.

FIG. 9 depicts details of a securable procedure kit ("kit") 310 according to one embodiment, including a substantially rigid or semi-rigid base, or body, 312 on which is included one or more pockets 316 in which kit components are removably disposed. Extensible legs 320 are attached to the body 312 so as to serve as a securing component in securing the kit 310 atop a structure in a desired location or position with respect to a clinician performing a medical procedure. A flexible drape 324 of a suitable drape material is also attached to the body 312 of the kit 310. The drape 324 can be unfolded/extended so as to provide a sterile barrier or isolation of the kit 310.

Figure 10A:
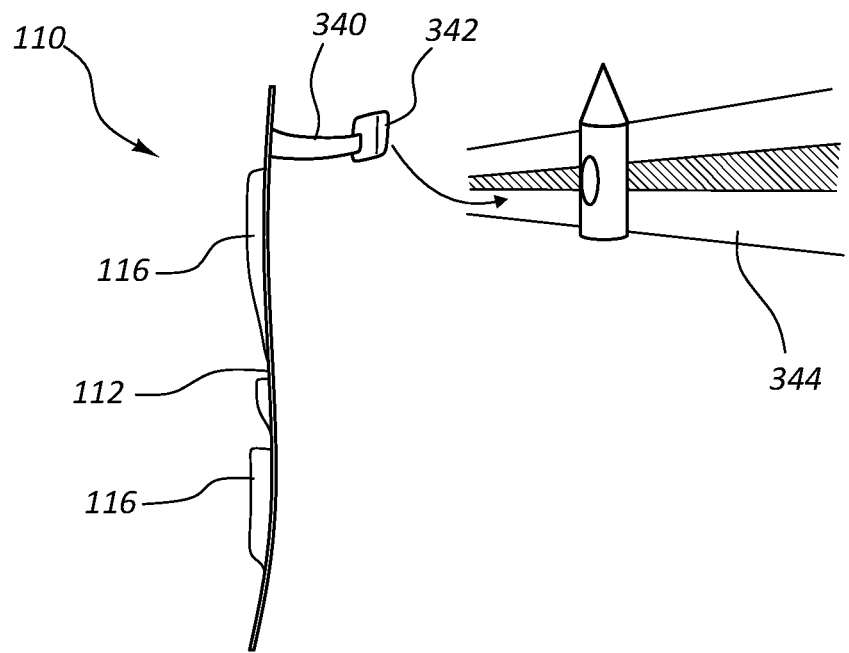
FIGS. 10A and 10B are various views of a securable procedure kit according to one embodiment.
Figure 10B:
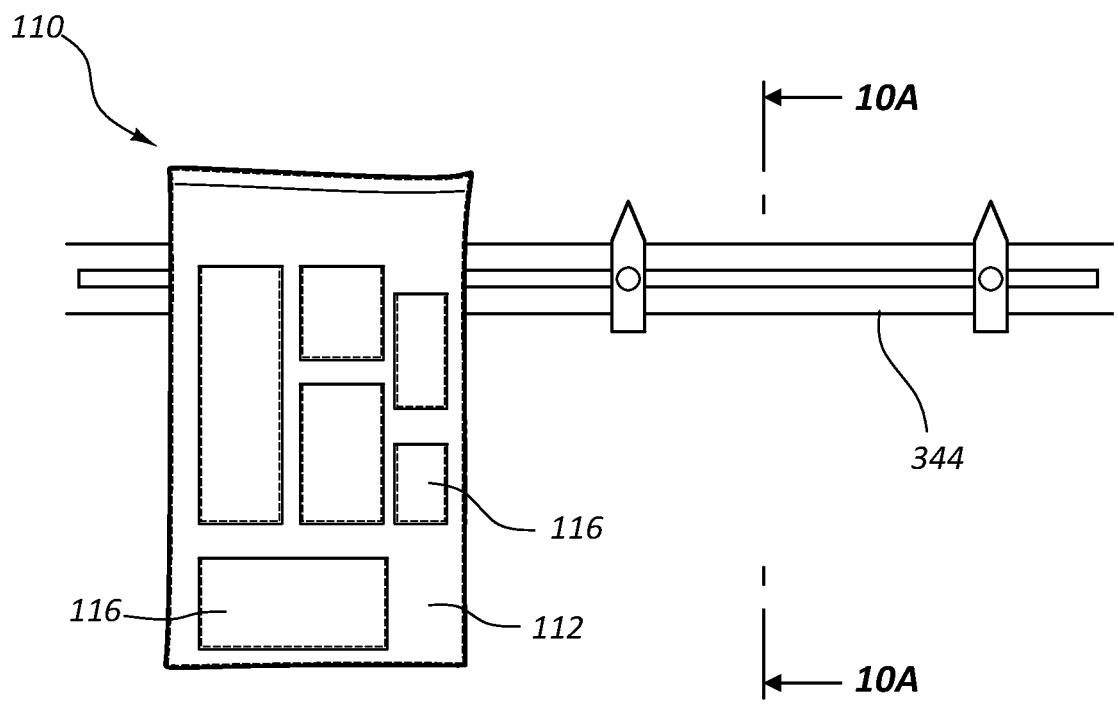

FIGS. 10A and 10B depict details of a securing component for the procedure kit 110 according to another embodiment, including a support rod 340 attached at one end to the kit body 112 and including at an opposite end a fitting 342 suitable for engaging an accessory rail 344 commonly located above patient beds in a hospital/procedure room setting. For instance, in the present embodiment, the fitting 342 is configured to fit into a channel of the accessory rail 344 so as to secure the kit 110 in a position proximate the patient bed, as desired. The particular configuration of the support rod 340 and fitting 342 can be varied to fit different accessory rail/other structure configurations.

Figure 11A:
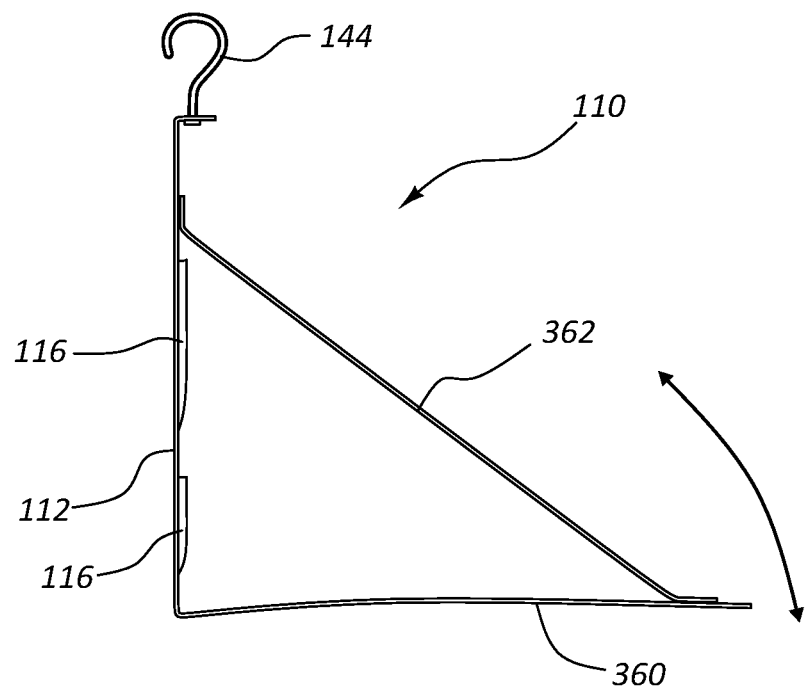
FIGS. 11A and 11B are various views of a securable procedure kit according to one embodiment.
Figure 11B:
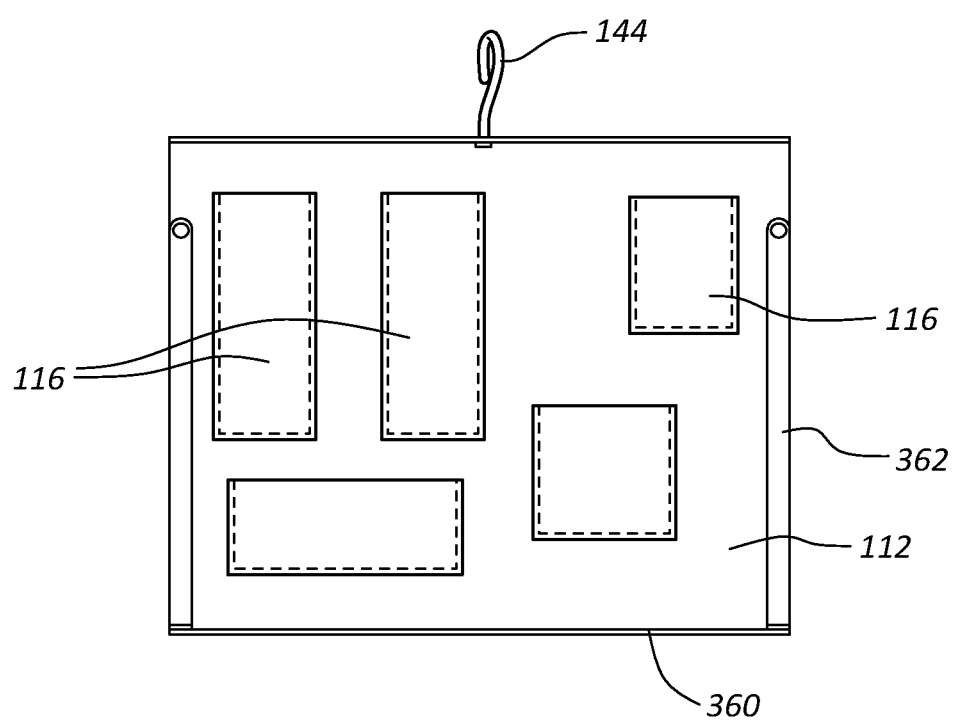

FIGS. 11A and 11B depict details of the procedure kit 110 according to another embodiment, wherein the body 112 of the kit includes a plurality of pockets 116 and a fold-out table 360 that is supported by two support cords 362. This enables the kit 110, the vertical upper portion of which is supported in place via the hanger hook 144, to provide a flat surface therebelow for use by the clinician during the medical procedure. As mentioned, the table 360 is foldable to enable the kit 110 to assume a substantially flat configuration for storage, etc. The size, shape, and other configuration of the fold-out table 360 can vary from what is shown and described herein.

Figure 12:
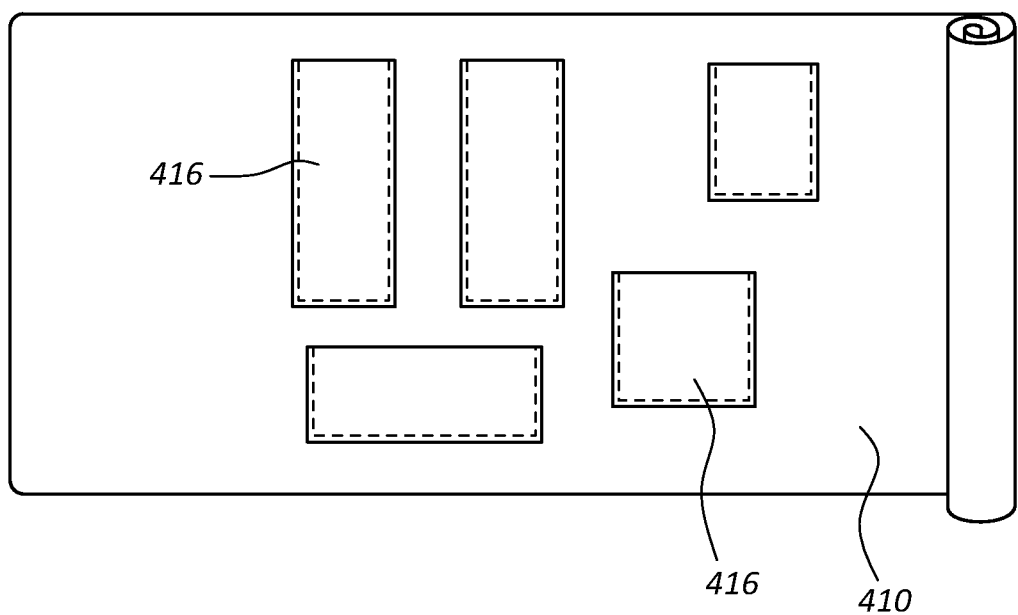
FIG. 12 is a top view of a procedure drape in accordance with one embodiment.

FIG. 12 depicts a procedure kit incorporated into a surgical/procedure drape 410 according to one embodiment, wherein a top surface of the drape includes a plurality of pockets 416 for removably receiving therein medical components. In this way, the drape 410 can be placed over the patient, with the medical components immediately at hand and accessible in the pockets 416. Of course, the size and shape of the drape and pockets can vary, and the drape can be folded or otherwise packed in a sterile package prior to use.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A procedure kit for use in a medical procedure on a patient, comprising:
   a body defining a pocket area, the pocket area including a partition that extends from a lower most perimeter to a height less than a height of the pocket area to define a plurality of pockets, each of the plurality of pockets sized to removably receive therein components for use in the medical procedure, wherein a first pocket has a first width and a second pocket has a second width less than the first width;
   an openable flap that covers at least a portion of the plurality of pockets;
   a first adhesive portion included on a portion of the body to enable the procedure kit to be secured to a structure or surface proximate to the patient; and a second adhesive portion to permanently seal the openable flap over the at least a portion of the plurality of pockets on a front face of the body.

2. The procedure kit as defined in claim 1, wherein the body is substantially flat at rest and flexible.

3. The procedure kit as defined in claim 2, wherein the body is substantially translucent.

4. The procedure kit as defined in claim 3, wherein the body includes polyethylene.

5. The procedure kit as defined in claim 1, wherein the plurality of pockets are disposed on the front face of the body and wherein the first adhesive portion is disposed on a rear face of the body.

6. The procedure kit as defined in claim 1, wherein the openable flap further includes a tear-away portion, the tear-away portion providing an access flap to the plurality of pockets when the tear-away portion is removed.

7. The procedure kit as defined in claim 1, wherein the components are employed to insert a catheter into a body of the patient.

8. The procedure kit as defined in claim 1, wherein the first adhesive portion is initially covered by a release strip, and wherein the first adhesive portion is used to secure the procedure kit to a drape covering the patient.

9. The procedure kit as defined in claim 1, wherein the first adhesive portion enables removal of the procedure kit from the structure or surface after the procedure kit is no longer needed.

10. A method for using a procedure kit in performing a medical procedure, the method comprising:
providing a procedure kit including a body defining a plurality of pockets, each of the plurality of pockets having removably disposed therein a component for use in the medical procedure, a first pocket of the plurality of pockets including a first width, and a second pocket of the plurality of pockets defining a second width less than half of the first width and designed to orient an elongate component along an axis, the body further including a first adhesive portion on an exterior portion thereof and a second adhesive portion to permanently seal a flap to at least a portion of the plurality of pockets;
securing the procedure kit with the first adhesive portion to a location proximate a patient; and
removing a tear-away portion of the flap to provide access to the components disposed in the plurality of pockets.

11. The method for using as defined in claim 10, further comprising removing the procedure kit from the location proximate the patient when no longer needed.

12. The method for using as defined in claim 10, wherein removing the tear-away portion occurs before securing the procedure kit.

13. The method for using as defined in claim 10, further comprising removing the procedure kit from a sterilized outer pouch before securing the procedure kit or removing the tear-away portion.

14. The method for using as defined in claim 10, wherein securing the procedure kit includes securing the procedure kit to a drape covering the patient.

15. A procedure kit for performing a medical procedure on a patient, comprising:
a flexible, substantially flat body;
a plurality of pockets disposed on a face of the body, each of the plurality of pockets sized to removably receive therein a component for use in the medical procedure;
a flexible fold-out tray included on the body being movable between a first position that is substantially parallel to the body, and a second position that is substantially perpendicular to the body, the flexible fold-out tray maintaining a substantially flat surface in both the first position and the second position; and
a securing component for securing the procedure kit in a desired position during the medical procedure.

16. The procedure kit as defined in claim 15, wherein each of the components are pre-disposed in the plurality of pockets at time of use of the procedure kit by a user.

17. The procedure kit as defined in claim 15, wherein the securing component includes at least one of a hook, a hole, an adhesive, a clip, a clamp, and a fitting for being received in a track of an accessory rail.

18. The procedure kit as defined in claim 15, wherein the plurality of pockets are oriented such that the procedure kit is suitable for hanging vertically.

19. The procedure kit as defined in claim 15, wherein the procedure kit includes a stiffening component such that the body retains its form when hung from a location.

20. The procedure kit as defined in claim 15, wherein the body includes at least one fastener for closing the body of the procedure kit.

21. The procedure kit as defined in claim 20, wherein the at least one fastener includes at least one of a button and a button hole, and a snap.

22. The procedure kit as defined in claim 15, wherein the flexible, fold out tray is integrally formed as part of the body.

23. The procedure kit as defined in claim 15, wherein the flexible, fold out tray is disposed at a bottom portion of the body and is supported by two support arms.

24. The procedure kit as defined in claim 15, wherein the plurality of pockets are included on a front face of the body and the securing component is included on a rear face of the body.

25. A drape for use in covering at least a portion of a body of a patient during a medical procedure, comprising:
a flexible drape portion including a drape material; and
a pocket integrally formed on a top surface of the flexible drape portion, the pocket including a partition that extends from a perimeter to a midpoint of the pocket to define two or more compartments sized to removably receive therein components for use in the medical procedure, at least one compartment of the two or more compartments designed to orient an elongate component along an axis;
an openable flap that covers at least a portion of the pocket; and
an adhesive portion to permanently seal the openable flap to at least a portion of the pocket on the flexible drape portion.

26. The drape as defined in claim 25, wherein the drape can be folded or rolled and packaged in a sterile package before use by a user.

27. The drape as defined in claim 25, wherein the openable flap further includes a tear-away portion, the tear-away portion providing an access flap to the pocket when the tear-away portion is removed.

* * * * *